US009678046B2

(12) United States Patent
Tolley et al.

(10) Patent No.: US 9,678,046 B2
(45) Date of Patent: Jun. 13, 2017

(54) GAS CHROMATOGRAPHY USING A THERMAL GRADIENT THAT IS SUBSTANTIALLY MONOTONICALLY NON-INCREASING AND HAS A POSITIVE SECOND DERIVATIVE

(71) Applicant: BRIGHAM YOUNG UNIVERSITY, Provo, UT (US)

(72) Inventors: H. Dennis Tolley, Mapleton, UT (US); Anzi Wang, Salt Lake City, UT (US); Samuel E. Tolley, Mapleton, UT (US); Milton L. Lee, Pleasant Grove, UT (US); Aaron R. Hawkins, Provo, UT (US)

(73) Assignee: BRIGHAM YOUNG UNIVERSITY, Provo, UT (US)

(*) Notice: Subject to any disclaimer, the term of this patent is extended or adjusted under 35 U.S.C. 154(b) by 0 days.

(21) Appl. No.: 14/488,013

(22) Filed: Sep. 16, 2014

(65) Prior Publication Data

US 2015/0075374 A1 Mar. 19, 2015

Related U.S. Application Data

(60) Provisional application No. 61/960,332, filed on Sep. 16, 2013, provisional application No. 61/960,329, filed on Sep. 16, 2013.

(51) Int. Cl.
*G01N 30/30* (2006.01)
*G01N 30/60* (2006.01)

(52) U.S. Cl.
CPC ......... *G01N 30/30* (2013.01); *G01N 30/6095* (2013.01); *G01N 2030/3015* (2013.01)

(58) Field of Classification Search
CPC ........... G01N 30/30; G01N 2030/3015; G01N 2030/3038; G01N 2030/3046; G01N 2030/3076
See application file for complete search history.

(56) References Cited

U.S. PATENT DOCUMENTS

| | | | |
|---|---|---|---|
| 3,023,835 A | 10/1958 | Brashear | |
| 3,043,127 A * | 7/1962 | De Ford | G01N 30/30 73/23.22 |
| 4,923,486 A | 5/1990 | Rubey | |
| 5,028,243 A | 7/1991 | Rubey | |
| 5,135,549 A * | 8/1992 | Phillips | G01N 30/30 210/198.2 |
| 5,215,556 A * | 6/1993 | Hiller | G01N 30/30 95/87 |
| 5,611,846 A | 3/1997 | Overton et al. | |
| 5,808,178 A | 9/1998 | Rounbehler | |
| 5,846,293 A * | 12/1998 | Rubey | G01N 30/06 73/23.26 |
| 9,310,343 B2 * | 4/2016 | Iso | G01N 30/30 |
| 2006/0054543 A1 | 3/2006 | Petro et al. | |
| 2009/0320560 A1 * | 12/2009 | Ross | G01N 30/30 73/23.39 |

FOREIGN PATENT DOCUMENTS

EP 0445967 A2 9/1991

OTHER PUBLICATIONS

Contreras, Jesse A. et al., Axial Temperature Gradients in Gas Chromatography, Department of Chemistry and Biochemistry, Brigham Young University, Dec. 2010.
Contreras, Jesse A. et al., Dynamic thermal gradient gas chromatography, Journal of Chromatography A, 1302 (Jun. 14, 2013) pp. 143-151.
Contreras, Jesse A. et al., Peak sweeping and gating using thermal gradient gas chromatography, Journal of Chromatography A, 1278 (Jan. 9, 2013) pp. 160-165.
Nerheim, A. G., Gas-Liquid Chromathermography. Anal. Chem. Mar. 1960, 32, 436-437.
Tudge, A. P., Studies in Chromatographic Transport III. Chromathermography. Can. J. Phy. Oct. 3, 1961, 40, 557-572.
Ohline, R. W.; DeFord, D. D., Chromathermography, the Application of Moving Thermal Gradients to Gas Liquid Partition Chromatography. Anal. Chem. Feb. 1963, 35, 227-234.
Kaiser, R. E., Enriching Volatile Compounds by a Temperature Gradient Tube. Anal. Chem., May 1973, 45, 965-967.
Fenimore, D. C., Gradient Temperature Programming of Short Capillary Columns. J. Chromatography. 1975, 112, 219-227.
Le Parlouer, P., et al., Gas Chromatography with Backflushing, with Linear Temperature Programming in the First Direction and a Programmed Longitudinal Positive Temperature Gradient During the Opposite Direction of Gas Flow. J. Chromatogr. A. 1977, 133, 253-261.
Berezkin, V. G., et al., Temperature Gradients in Gas Chromatography. J. Chromatogr. 1986, 373, 21-44.
Zhao, H., et al., Characteristics of TGPGC on Short Micro Packed Capillary Column. Anal. Sci., Jan. 2002, 18, 93-95.
Rubey, W. A., A Different Operational Mode for Addressing the General Elution Problem in Rapid Analysis Gas Chromatography. J. High Resolut. Chromatogr. 1991, 14, 542-548.
Rubey, W., Operational Theory and Instrumental Implementation of the Thermal Gradient Programmed Gas Chromatography (TGPGC) Mode Analysis. J. High Resolut. Chromatogr. 1992, 15, 795-799.

(Continued)

*Primary Examiner* — Robert Clemente
(74) *Attorney, Agent, or Firm* — Morriss O'Bryant Compagni, PC

(57) ABSTRACT

A system and method for thermal gradient gas chromatography wherein a front or injection end of a column is heated to a higher temperature than a back or detector end to thereby create a thermal gradient having a profile that is substantially monotonically non-increasing and has a positive second derivative, and then providing a heat source to raise the thermal gradient and cause it to remain stationary or to travel through the column while maintaining a desired profile.

21 Claims, 9 Drawing Sheets

(56) References Cited

OTHER PUBLICATIONS

Phillips, J. B.; Jain, V., On-Column Temperature Programming in Gas Chromatography Using Temperature Gradients Along the Capillary Column. J. Chromatogr. Sci. 1995, 33, 543-550.

Jain, V.; Phillips, J. B., High-Speed Gas Chromatography Using Simultaneous Temperature Gradient in Both Time and Distance along Narrow-Bore Capillary Columns. J. Chromatogr. Sci. 1995, 33, 601-605.

Leslie S. Ettre et al: "A. A. Zhukhovitskii—A Russian Pioneer of Gas Chromatography", LCGC Chromatographyonline, Nov. 1, 2000, pp. 1148-1155, Retrieved from the Internet: URL:http://images.alfresco.advanstar.com/alfresco_images/pharma/2014/08/22/599306fl-ba62-4563-8536-2603d21e7e84/article-14545.pdf.

* cited by examiner

GAS CHROMATOGRAPHY USING A THERMAL GRADIENT THAT IS SUBSTANTIALLY MONOTONICALLY NON-INCREASING AND HAS A POSITIVE SECOND DERIVATIVE

BACKGROUND

Description of Related Art

Gas chromatography (GC) may be a widely used analytical technique for the analysis of gases, and volatile and semi-volatile organic compounds, due to its simplicity, high separation efficiency and relatively short analysis time.

FIG. 1 is a block diagram that is provided to show that some of the principle components of a GC system may be described as a tube, channel or column 10 (hereinafter referred to as a "column"), an injector 12 by which a sample may be injected into the column, a temperature regulation system 14 with which the temperature of the column may be established and controlled through the duration of a separation process, and a detector 16 that may detect analytes eluting from the column. It should be understood that there are many modifications that may be made to the system shown in FIG. 1 without departing from the subject matter of the invention.

The process of controlling the temperature within the column 10 may be controlled by a computer to ensure that the temperature at any point in time is at a predetermined set value. The temperature regulation system 14 that may be used to heat the column 10 and to maintain the column at a specific temperature may be an oven. However, other temperature regulation systems include but should not be considered as limited to vapor jackets, oil baths, Dewar flasks, heat exchanger, air bath oven, resistive heating, infra-red heating, inductive heating and microwave heating.

There are different implementations of GC, including isothermal where the column temperature is held fixed for the entire separation, and programmed temperature where the entire column is gradually heated throughout the separation to increase the column temperature in a predetermined, programmed manner. What is important to understand about these prior art methods is that the temperature of the column is substantially uniform along its entire length. In other words, variations in temperature may only be unintentional or caused by limitations of the heating method being used.

BRIEF SUMMARY

The present invention is a system and method for thermal gradient gas chromatography wherein a front or injection end of a column is heated to a higher temperature than a back or detector end to thereby create a thermal gradient having a profile that is substantially monotonically non-increasing and has a substantially non-negative second derivative, and then providing a heat source to shift upward the thermal gradient, wherein the thermal gradient may include a finite portion where the thermal gradient may be strictly negative.

In a first aspect of the invention, a gas chromatograph is provided that includes an injector, a column and a detector, with the column having a front end for receiving a sample from the injector, and a back end for elution of the sample into the detector.

In a second aspect of the invention, a first heating device is used for applying primary heat to the column to create a thermal gradient along at least a portion of the column, and wherein at least some portion of the thermal gradient is negative.

In a third aspect of the invention, a second heating device is used for applying secondary heat to the column to thereby raise, translate or shift upwards the thermal gradient of the column.

In a fourth aspect of the invention, the thermal gradient is substantially monotonically non-increasing and the thermal gradient has a substantially non-negative second derivative.

These and other embodiments of the present invention will become apparent to those skilled in the art from a consideration of the following detailed description taken in combination with the accompanying drawings.

DETAILED DESCRIPTION

Reference will now be made to the drawings in which the various embodiments of the present invention will be given numerical designations and in which the embodiments will be discussed so as to enable one skilled in the art to make and use the invention. It is to be understood that the following description illustrates embodiments of the present invention, and should not be viewed as narrowing the claims which follow.

The first embodiment of the present invention is the creation of a desired thermal gradient within a column. It is understood that there may be many different hardware configurations of a gas chromatograph that may be constructed in order to achieve the desired thermal gradient profile. Accordingly, the first embodiment should not be considered to be limited to any particular hardware configuration, but only to a gas chromatograph that can achieve the desired thermal gradient profile.

Figure 1:
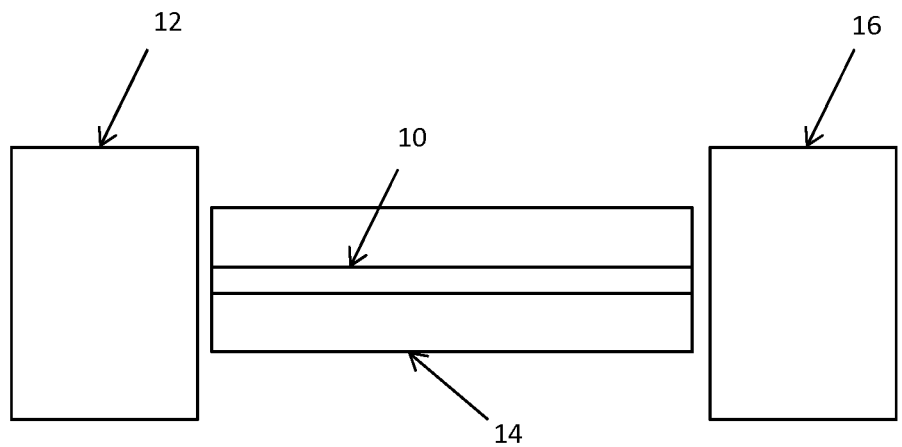
FIG. 1 is a block diagram of the components that may be part of a gas chromatography system in the prior art.
Figure 2:
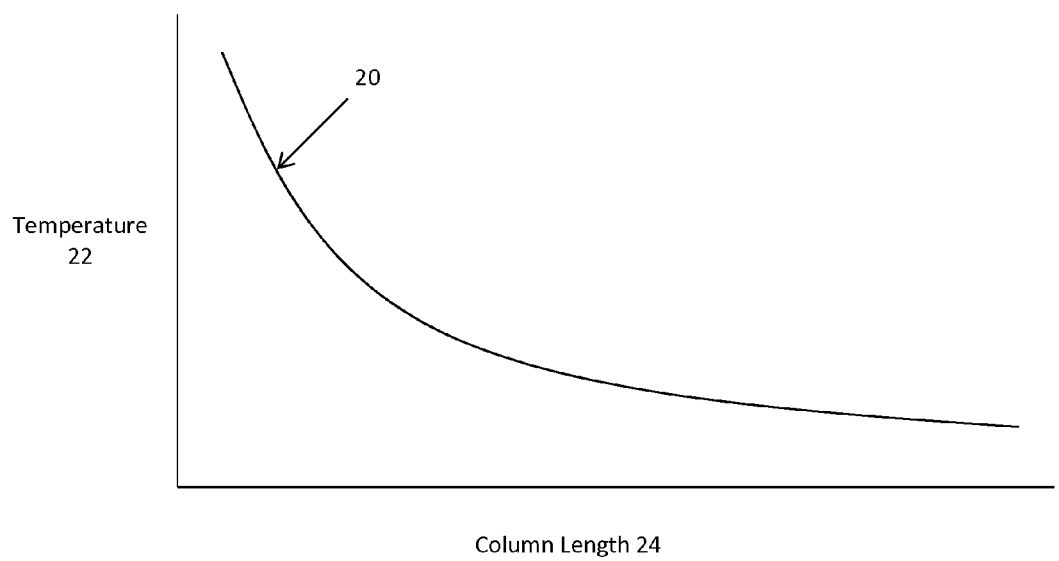
FIG. 2 is an example of a thermal gradient curve of a first embodiment that has a smooth curve.

FIG. 2 is a graph of a first embodiment of a desired thermal gradient as represented by a thermal gradient profile. The graph shows a thermal gradient curve 20 as a function of a length 24 of a column of a gas chromatograph on an X axis, with temperature value being given on the Y axis.

Figure 3:
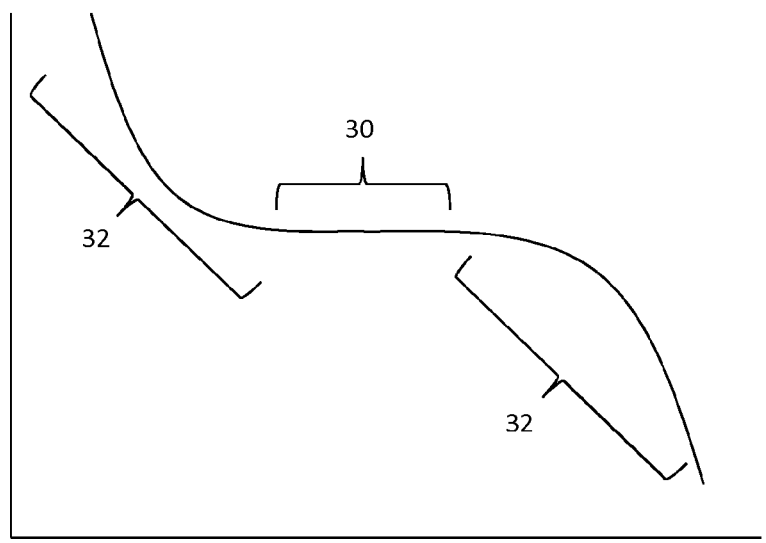
FIG. 3 is a graph of a thermal gradient curve of a first embodiment where the thermal gradient curve has segments that are linear or non-increasing.

The thermal gradient curve 20 may have several desired characteristics. A first characteristic of the thermal gradient curve 20 may be that the curve is monotonically non-increasing, also referred to as monotonically decreasing. This document defines monotonically non-increasing as shown in FIG. 3 where the curve may include segments that are linear and non-increasing 30, as well as segments that are decreasing 32. However, this document also chooses to define the desired thermal gradient as "substantially" monotonically non-increasing as shown in FIG. 4.

Figure 4:
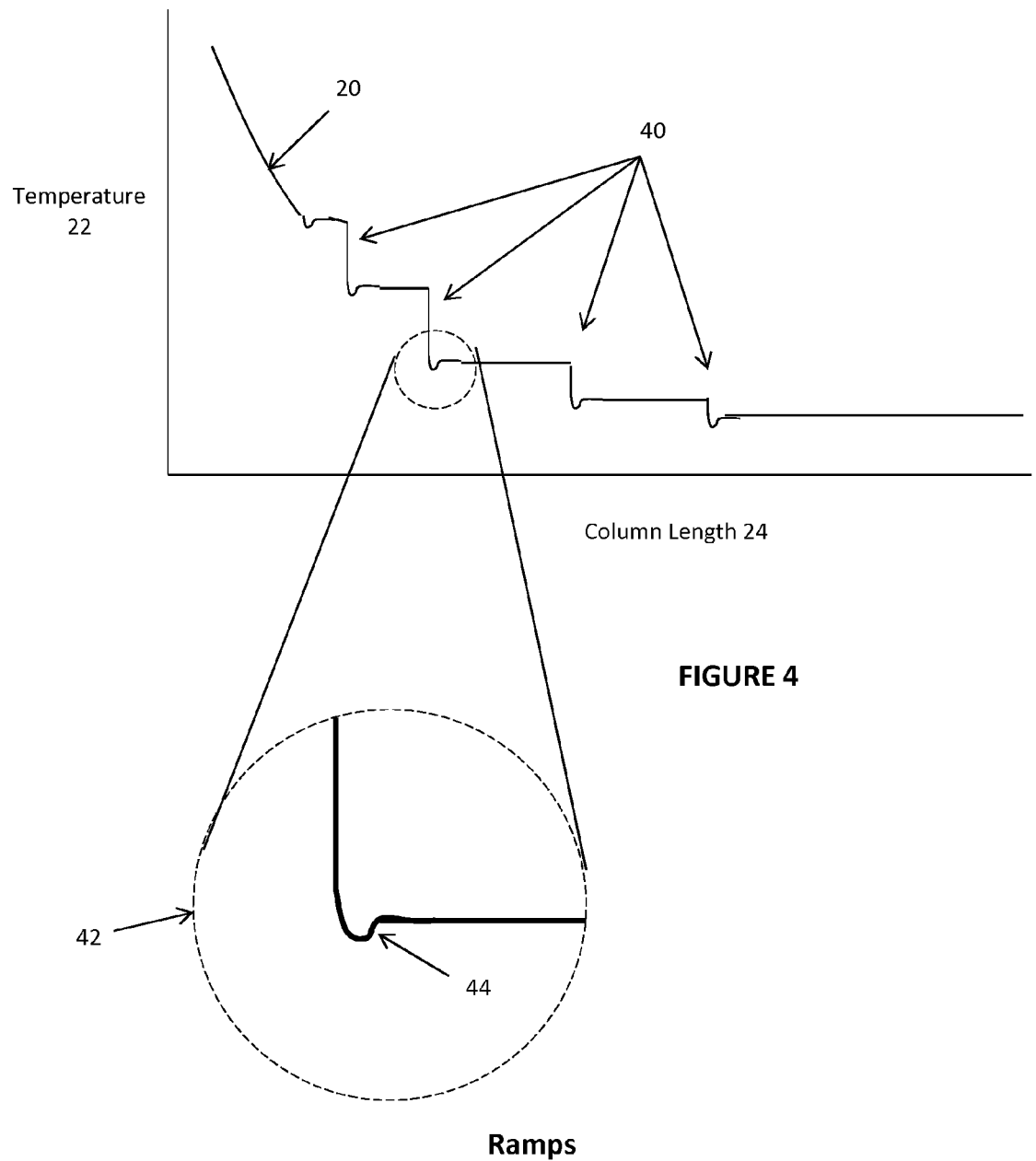
FIG. 4 is a graph of a thermal gradient curve that is comprised of piece-wise or step-wise linear segments and that has at least one segment that is increasing.

To illustrate this concept, FIG. 4 is provided as another illustration of the thermal gradient curve 20 that may be comprised of piece-wise or step-wise linear segments 40. The step-wise linear segments 40 may be non-increasing as shown. The overall thermal gradient curve 20 is substantially monotonically non-increasing while also formed from a plurality of step-wise linear segments 40. This figure is an example only and should not be considered limiting regarding the number or length of step-wise linear segments that may be used to form the thermal gradient curve 20.

FIG. 4 also illustrates another feature of the first embodiment. The phrase "substantially monotonically non-increasing" is defined herein as a thermal gradient curve 20 that overall is monotonically non-increasing. However, there may be relatively short segments 44 in the thermal gradient curve 20, relative to the entire length of the curve, that are increasing as shown within circle 42. However, these short segments 44 that are increasing may be relatively short compared to the total length of the thermal gradient curve 20, and therefore may not effect operation of the thermal gradient gas chromatograph. Accordingly, while the thermal gradient curve 20 may not be strictly monotonically non-increasing, by choosing to describe the curve as "substantially" monotonically non-increasing, this serves the purpose of allowing for short segments 44 that are actually increasing even though the overall thermal gradient curve 20 is decreasing.

What is important to this first embodiment is that the temperature generally or substantially decreases with distance when moving from the front end to the back end of the column. Nevertheless, the definition of the substantially monotonically non-increasing thermal gradient curve with a positive second derivative may also include exceptions where there are short segments or portions of the column where the temperature increases for a short length and where the second derivative of the thermal gradient curve may be strictly negative. Accordingly, the phrase "substantially monotonically non-increasing" may be used within this document to describe such a thermal gradient curve as well as a curve that has substantially a non-negative second derivative.

Figure 5:
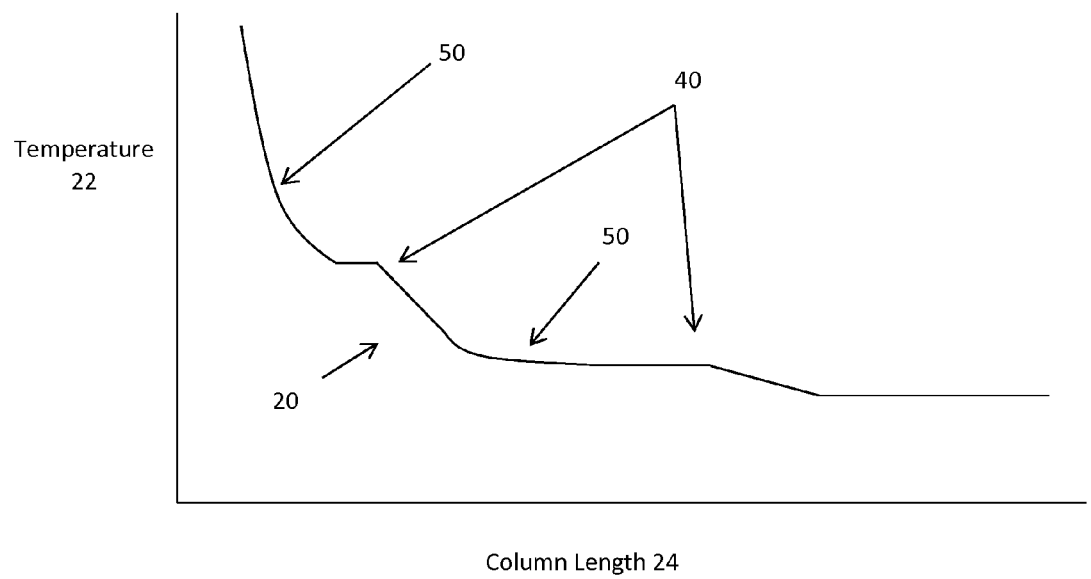
FIG. 5 is a graph of a thermal gradient curve that is comprised of a combination of smooth segments and piece-wise or step-wise linear segments.

FIG. 5 is an example of a thermal gradient curve 20 that may be comprised of a combination of curving or arcuate segments 50 and step-wise linear segments 40. This figure is an example only and should not be considered limiting regarding the number of arcuate segments 50 and step-wise linear segments 40 that may be part of the thermal gradient curve 20.

It was stated earlier that the thermal gradient curve 20 may be defined as a curve that has a positive second derivative. The second derivative measures how the rate of change of a quantity is itself changing. On the graph of a function, the second derivative corresponds to the curvature of the graph. Accordingly, the second derivative of the thermal gradient curve 20 of the first embodiment may be positive.

Another feature of the first embodiment of the invention may be that the profile of the thermal gradient curve 20 may be raised or shifted upward while the defining characteristics of the thermal gradient curve 20 are not changed. For example, consider FIG. 6 which shows the thermal gradient curve 20 in a first position 60 on the graph. Additional heat may then be applied to the entire column to cause a shift upward in the position of the thermal gradient curve 20 to a new position 62. In effect, the thermal gradient curve may be translated upward with no other modification of its profile.

In other words, primary heat from a primary heat source has already been applied to the column to create the profile or shape of the thermal gradient curve 20. This additional or secondary heat is applied from a secondary heat source at the same time as the primary heat. The effect of applying the secondary heat equally across the entire column may be to cause an upward shift of the entire thermal gradient curve 20 with or without changing the shape or profile.

It may be important that the secondary heat be applied in a systematic way. A systematic way includes but should not be considered as limited to a controlled application of the primary heat, the secondary heat or both in order to manipulate the profile of the thermal gradient. For example, the secondary heat may be controlled in order to modify a rate at which the secondary heat raises or shifts upward the profile of the thermal gradient. Control of the thermal gradient may be accomplished according to a pre-defined set of criteria.

The primary heat is applied to the column as different amounts of heat applied to different locations to thereby form the thermal gradient. The most heat is applied to the front end of the column, and then less and less heat is gradually applied to the column until reaching the back end. The primary heat may be applied as discrete segments that may result in a thermal gradient forming from a plurality of step-wise segments or linear segments. Alternatively, the primary heat may be applied with smaller discrete segments that may cause the thermal gradient to have a smooth or arcuate and not a step-wise or linear appearance. Alternatively, the primary heat may be applied to create a combination of arcuate segments and discrete step-wise or linear segments.

Figure 6:
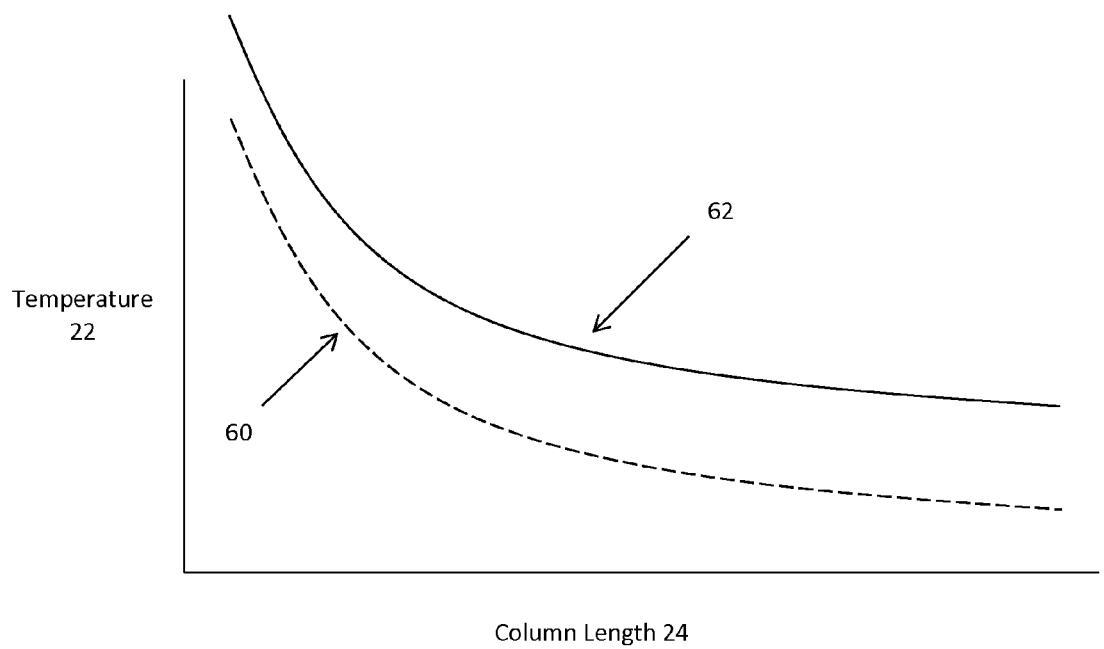
FIG. 6 is a graph of a thermal gradient curve that is shifted upwards while maintaining the original profile.

In contrast, the secondary heat may be substantially uniform along the entire length of the column. Accordingly, the thermal gradient curve 20 may be shifted upwards in temperature as shown in FIG. 6. FIG. 6 shows an original position 60 without the secondary heat applied and the new position 62 of the thermal gradient curve 20 after the secondary heat is applied. The shift upwards of the thermal gradient curve 20 may be accomplished by any appropriate heating mechanism.

When it is time to detect compounds, the compounds are eluted from the column into a detector. This may be accomplished by raising the thermal gradient in the column in a systematic manner. It is believed that there may be advantages of systematic or programmed patterns of constructing and raising the thermal gradient within the column as the compounds are eluted. For example, as a compound is eluting from the column, a front edge of a peak may be at a lower temperature than a back end of the peak. This may cause the back end of the peak to have a velocity that is higher than the front end. A result of this difference in speed may be a compression of the peaks as they reach the end of the column. This may result in better separation of compounds because of narrower peaks, and increased sensitivity because the peaks may be higher and more symmetrical.

Another result of the first embodiment may be the preservation of the profile of the thermal gradient curve 20 as the compounds are moved through the column. In contrast, other prior art methods may destroy the thermal gradient by bringing the compounds in the column to an isothermal state or equilibrium.

It should be mentioned that the first embodiment may also be capable of being flexible in the profile of the thermal gradient curve 20. In other words, while the profile of the thermal gradient may be shifted upwards by applying the secondary heat, substantially preserving the profile in the column, the thermal gradient in the column may also be modified, adjusted or otherwise changed without losing the characteristics of being substantially monotonically non-increasing and having a positive second derivative. Accordingly, it should be considered within the scope of the invention to allow for changes or modifications to the thermal gradient as it is held stationary or as it is raised by the secondary heat.

Figure 7:
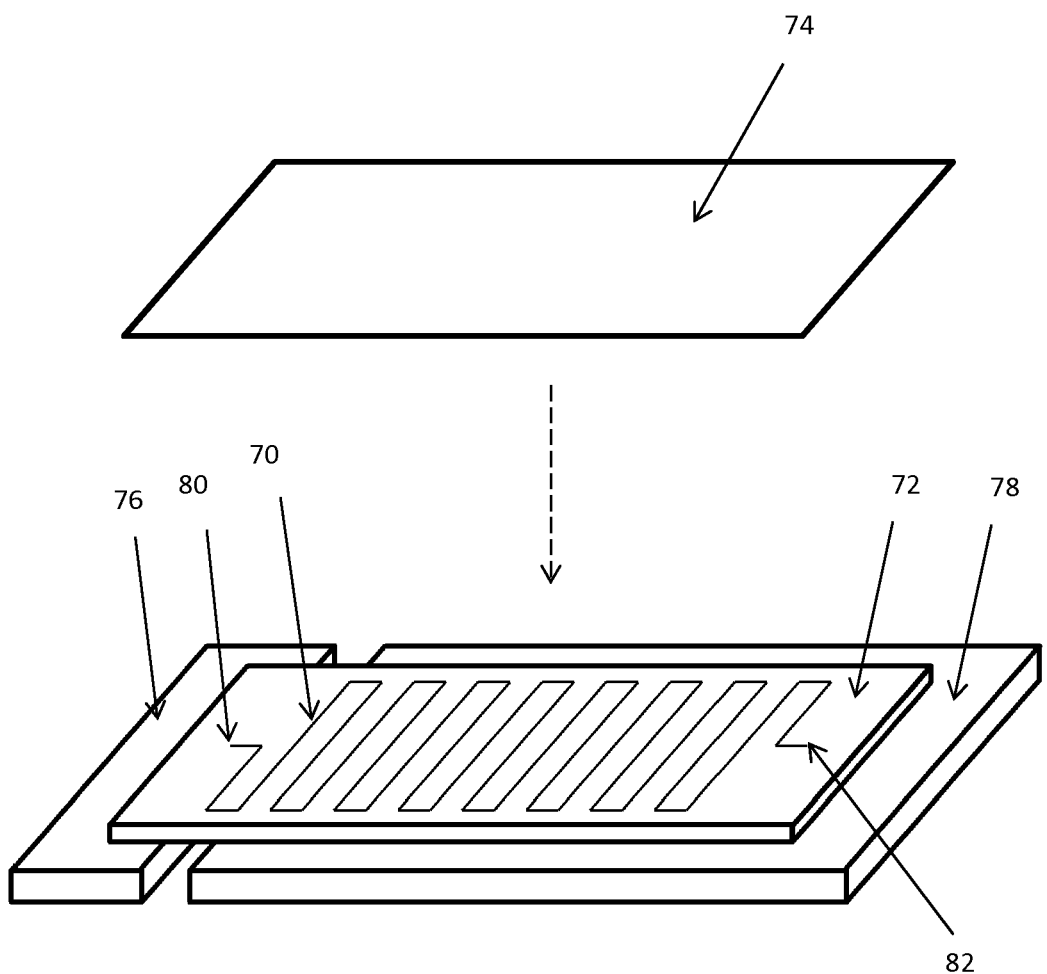
FIG. 7 is provided as a perspective view of a first column and substrate of a thermal gradient GC that can be used to create the desired thermal gradient.

FIG. 7 is provided to illustrate one example of hardware that may be used for the column and heating sources that may be used to create the desired thermal gradient in a gas chromatograph of the invention. FIG. 7 shows a first embodiment of a planar configuration for a column 70. The column 70 may be formed in a planar configuration in order to enable uniform heating of the column 70.

The column 70 may be formed in an appropriate material by forming a channel or column in a planar substrate material 72, and then a covering or top layer 74 may be disposed over the planar substrate material as indicated by the dotted arrow. For example, the column 70 may be formed using etching, a laser, or any other means that may remove material from the planar substrate material 72.

The length, width and depth of the column 70 may be manufactured using appropriate dimensions as understood by those skilled in the art. The length of the column 70 may be any desired length from 10 centimeters to 50 meters because the principles of the first embodiment are adaptable to different length columns. What may be important in this first embodiment is that the column 70 be disposed in the planar substrate material 72 so that a heating mechanism may then be disposed underneath, above, around, on a side or any other location that the heating mechanism may be disposed in order to uniformly heat the entire channel 70 when applying the secondary heat. For example, the heating mechanism may operate like a hot plate or an oven. However, this example should not be considered as limiting, and any heating method that will uniformly apply the secondary heat to the entire column 70 may be used and fall within the scope of the first embodiment.

FIG. 7 is provided as a perspective view of a portion of the GC and includes a first heating source 76 and a second heating source 78. The first heating source 76 is shown disposed and underneath a front end 80 or injection end of the column 70. The second heating source 78 is shown disposed underneath and along a length of the column 70, including at the back end 82 or ejection end. The first heat source 76 may be considered to be the primary heat source that is used to create the thermal gradient within the column 70. The secondary heat source 78 may be the secondary heat that is applied to the column to modify the thermal gradient once it is created.

The shape of the channel 70 in the planar substrate material 72 may be any desired shape including, but not limited to a spiral, a serpentine shape or any other shape that will provide a desired length of the column and enable the application of the primary heat in order to create the thermal gradient curve and application of the secondary heating if needed. FIG. 7 shows that column 70 is formed as a serpentine shape in order to make the column as long as possible for the given width and length of the substrate material 72.

The primary heat and the secondary heat may be applied to the column 70 using any prior art method including, but should not be considered as limited to a heat exchanger, an air bath oven, resistive heating, infra-red heating, inductive heating and microwave heating as understood by those skilled in the art. The examples of the first heating source 76 and the secondary heating source 78 are for illustration purposes only and should not be considered as limited by the figure.

Figure 8:
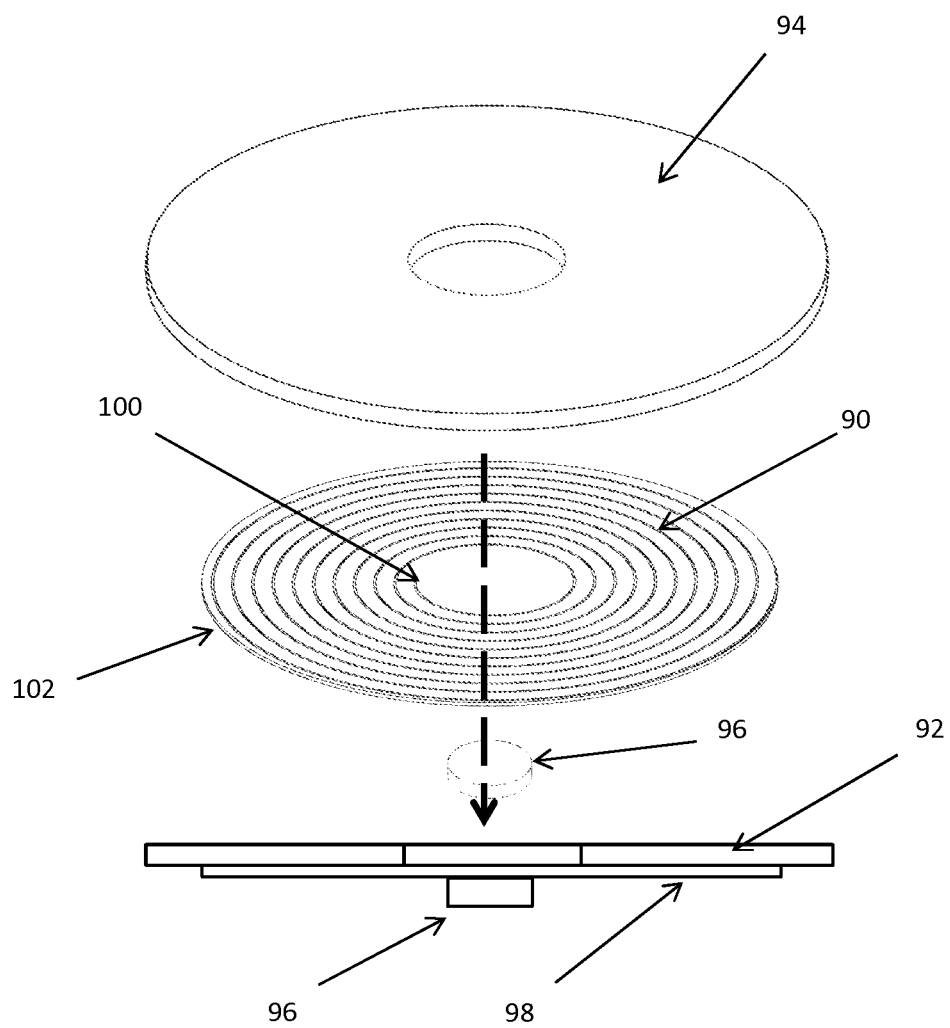
FIG. 8 is provided as a perspective and profile view of a second column and substrate of a thermal gradient GC that can also be used to create the desired thermal gradient.

FIG. 8 is provided as a perspective view and a profile view of a portion of the GC and includes a first heat source 96 and a second heating source 98. The first heating source 96 is shown disposed and underneath a front end 100 or injection end of the column 90, where the column begins at the center of a spiral. The second heating source 98 is shown disposed underneath and along a length of the column 90, including at the back end 102 or ejection end. The first heat source 96 may be considered to be the primary heat source that is used to create the thermal gradient within the column 90. The secondary heat source 98 may be the secondary heat that is applied to the column to modify the thermal gradient once it is created.

The shape of the channel 90 in the planar substrate material 92 may be any desired shape including, but not limited to a spiral, a serpentine shape or any other shape that will provide a desired length of the column and enable the application of the primary heat in order to create the thermal gradient curve and application of the secondary heating if needed. FIG. 8 shows that column 90 is formed as a spiral shape in order to make the column as long as possible for the given shape of the substrate material 92.

The column 90 may be formed in an appropriate material by forming a channel or column in the planar substrate material 92, and then a covering or top layer 94 may be disposed over the planar substrate material as indicated by the dotted arrow. For example, the column 90 may be formed using etching, a laser, or any other means that may remove material from the planar substrate material 92.

The manufacturing of the column in the substrate material may be performed using either macrofabrication or microfabrication technologies as is known to those skilled in the art. In other words, fabrication techniques may be applied from either or both macrofabrication and microfabrication technologies.

An aspect of the first embodiment may be the ability to use a column from the prior art. For example, previous columns in gas chromatographs include short column, long column, packed column and unpacked column designs. It should be understood that the first embodiment may be used with any of the prior art column designs to achieve the desired thermal gradient within the column.

Another aspect of the first embodiment is modification of the thermal gradient to alter either the rate at which the thermal gradient is shifted up or to make changes in the profile at different locations along the column. For example, such modifications to the profile may include changing a slope of the thermal gradient or changing the curvature, but other changes should also be considered to fall within the first embodiment of the invention.

Modifications of the thermal gradient may be designed to change one or more aspects of the GC including but not limited to resolution, efficiency, sharpness of the eluting peak or elution time. Such modifications may be done during a separation or in sequential separations.

A second embodiment of the present invention may be defined as a thermal gradient that is different from the thermal gradient of the first embodiment. However, the same thermal gradient GC may be used to create all the thermal gradients described in this document.

Figure 9:
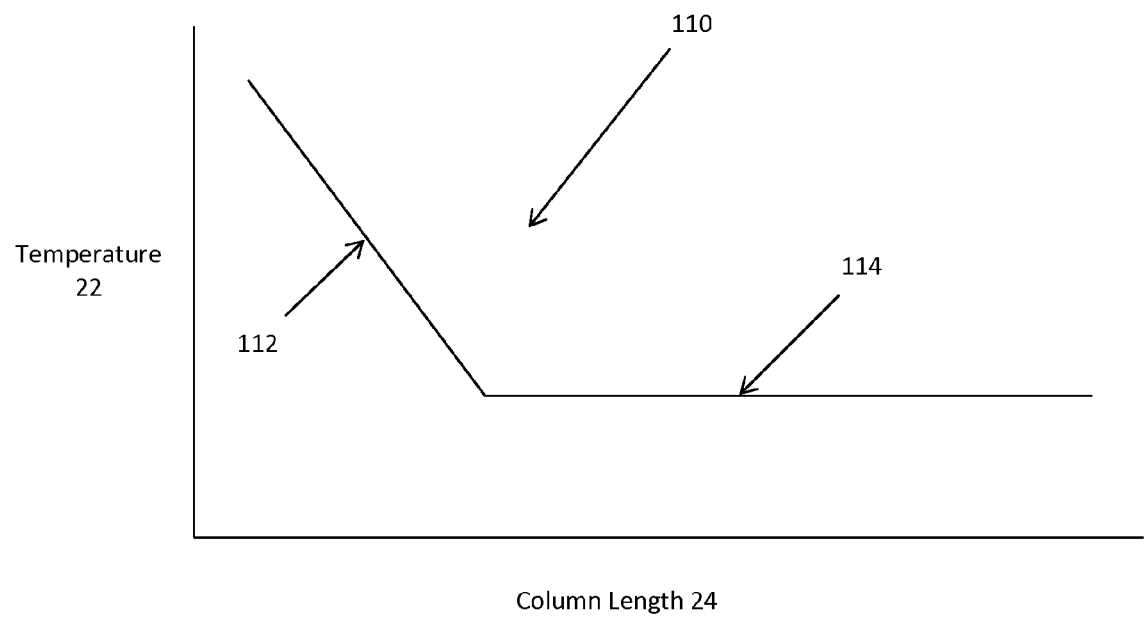
FIG. 9 is a graph of a thermal gradient curve having a first section with a linear negative slope and a second section that is isothermal.

The thermal gradient of the second embodiment may be defined in terms a second thermal gradient being represented by a second thermal gradient curve 110 having a first section 112 that has a non-negative second derivative, and having a first derivative that is non-positive. Thus the first section 112 may appear as shown in FIG. 9. FIG. 9 shows that the first section 112 may be linear and decreasing. The second section 114 of the second thermal gradient curve 110 may be flat or isothermal.

A third thermal gradient that is represented by a third thermal gradient curve. The third thermal gradient curve may have a first section that has a first derivative that is negative and a second section that has a non-negative second derivative.

Another aspect of the invention may be that as long as a thermal gradient exists over some portion of a column, then a thermal gradient exists that may provide the advantages of the present invention. The thermal gradient may be relatively small and may exist over a relatively short length of the column. The thermal gradient may be an arcuate slope, a linear slope or a step-wise function, or a combination of these profiles, and may be considered to be within the scope of the present invention.

These modifications of the thermal profile may be based on expected patterns of analytes in the sample, results of previous separations or real-time feedback of elution patterns in a current separation. Such feedback, either from previous runs of the GC, from statistical likelihood of a profile of analytes, or real-time closed loop feedback may be designed to improve estimates of retention time and quantitation as well as search for co-eluting contaminant peaks.

Those skilled in the art will readily appreciate that many modifications are possible in the example embodiments without materially departing from this first embodiment or the invention. Accordingly, all such modifications are intended to be included within the scope of this disclosure as defined in the following claims. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for performing gas chromatography, said method comprising:
   providing an injector, a column and a detector, the column having a front end for receiving a sample from the injector, and a back end for elution of the sample into the detector;
   providing a first heating device for applying primary heat to the column to create a monotonically decreasing and continuous thermal gradient along a portion of the column;
   providing a second heating device for applying secondary heat to the entire length of the column to thereby raise the thermal gradient of the column and overlap the first heating device; and
   wherein the thermal gradient is substantially non-linear and wherein the thermal gradient has a substantially non-negative second derivative.

2. The method as defined in claim 1 wherein the method of applying the secondary heat to thereby uniformly raise the thermal gradient of the column further comprises controlling the profile of the thermal gradient.

3. The method as defined in claim 2 wherein the method of controlling the profile of the thermal gradient further comprises causing the thermal gradient to maintain the desired profile while translating the thermal gradient to a higher temperature.

4. The method as defined in claim 2 wherein the method further comprises modifying a rate at which the secondary heat translates the thermal gradient to a higher temperature.

5. The method as defined in claim 1 wherein the method of creating the thermal gradient further comprises creating the thermal gradient having at least one segment that is linear.

6. The method as defined in claim 1 wherein the method of creating the thermal gradient further comprises creating the thermal gradient having a plurality of linear segments.

7. The method as defined in claim 1 wherein the method of creating the thermal gradient further comprises creating the thermal gradient from a plurality of step-wise linear segments.

8. The method as defined in claim 1 wherein the method of creating the thermal gradient further comprises creating the thermal gradient having at least one segment that is increasing without changing the thermal gradient from being substantially monotonically non-increasing and having a substantially non-negative second derivative.

9. The method as defined in claim 1 wherein the method of creating the thermal gradient further comprises preserving the thermal gradient within the column.

10. The method as defined in claim 1 wherein the method further comprises applying the secondary heat uniformly along a length of the column to thereby raise the thermal gradient.

11. The method as defined in claim 10 wherein the method of applying the secondary heat uniformly along a length of the column to thereby raise the thermal gradient further comprises preserving a profile of the thermal gradient.

12. The method as defined in claim 1 wherein the method further comprises modifying the thermal gradient along a length of the column by modifying the primary heat, modifying the secondary heat or a combination of modifying the primary heat and the secondary heat.

13. The method as defined in claim 1 wherein the method further comprises:
   obtaining compression of peaks of the compounds at the end of the column; and
   eluting the compounds from the column and into the detector.

14. The method as defined in claim 1 wherein the method further comprises:
   eluting the compounds from the column and into the detector; and
   obtaining increased sensitivity because the peaks of the compounds may be higher and more symmetrical when analyzed by the detector.

15. The method as defined in claim 1 wherein the method further comprises:
   providing a planar substrate material as a substrate for the column;
   removing material from a top surface of the planar substrate material to thereby form the column in the top surface; and disposing a cover over the top surface of the substrate material to complete formation of the column in the planar substrate material.

16. The method as defined in claim 15 wherein the method further comprises:
providing a primary heat source to apply the primary heat to the planar substrate material to thereby create the thermal gradient; and
providing a secondary heat source to apply the secondary heat to the planar substrate material to thereby modify the thermal gradient.

17. The method as defined in claim 1 wherein the method further comprises modifying the thermal gradient to thereby obtain different results from the GC, wherein modifying the thermal gradient may produce changes in resolution, efficiency, sharpness of the eluting peaks and elution times.

18. A method for performing gas chromatography, said method comprising:
providing an injector, a column and a detector, the column having a front end for receiving a sample from the injector, and a back end for ejection of the sample into the detector;
providing a first heating device for applying primary heat to the column to create a monotonically decreasing and continuous thermal gradient along a portion of the column;
providing a second heating device for applying secondary heat to the entire length of the column to thereby uniformly raise the thermal gradient of the column and overlap the first heating device; and
wherein the thermal gradient has a first segment that is substantially non-linear and wherein the thermal gradient has a substantially non-negative second derivative, has a first derivative that is non-positive with a portion of the thermal gradient having a negative first derivative, and has a second segment that is isothermal.

19. The method as defined in claim 18 wherein the method of applying the secondary heat to thereby uniformly raise the thermal gradient of the column further comprises controlling the profile of the thermal gradient.

20. The method as defined in claim 19 wherein the method of controlling the profile of the thermal gradient further comprises causing the thermal gradient to maintain the desired profile.

21. A method for performing gas chromatography, said method comprising:
providing an injector, a column and a detector, the column having a front end for receiving a sample from the injector, and a back end for elution of the sample into the detector, providing a planar substrate material as a substrate for the column, removing material from a top surface of the planar substrate material to thereby form the column in the top surface, and disposing a cover over the top surface of the substrate material to complete formation of the column in the planar substrate material;
providing a first heating device for applying primary heat to the column to create a monotonically decreasing and continuous thermal gradient along a portion of the column;
providing a second heating device for applying secondary heat to the entire length of the column to thereby raise the thermal gradient of the column and overlap the first heating device; and
wherein the thermal gradient is substantially non-linear and wherein the thermal gradient has a substantially non-negative second derivative.

* * * * *